(12) United States Patent
Jacobs et al.

(10) Patent No.: US 7,569,189 B2
(45) Date of Patent: Aug. 4, 2009

(54) OPENING AND CLOSING A CONTAINER

(75) Inventors: Merrit N. Jacobs, Fairport, NY (US); Robert A. Burkovich, Pittsford, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 786 days.

(21) Appl. No.: 11/093,606

(22) Filed: Mar. 30, 2005

(65) Prior Publication Data

US 2006/0228262 A1 Oct. 12, 2006

(51) Int. Cl.
*B01L 3/00* (2006.01)

(52) U.S. Cl. .............. 422/102; 422/100; 422/101; 422/63; 422/64; 422/65; 436/43; 436/47; 436/49; 436/130; 215/236; 220/810; 220/811; 220/812; 81/3.2; 81/3.31; 81/3.33; 81/3.09

(58) Field of Classification Search ............. 422/63–65; 222/129

See application file for complete search history.

(56) References Cited

U.S. PATENT DOCUMENTS 4,762,029 A 8/1988 Chen (Continued)

FOREIGN PATENT DOCUMENTS

CA 2305990 * 10/2000

(Continued)

OTHER PUBLICATIONS

European Search Report, dated Jun. 28, 2006, for European Appln. No. EP 06251718.

(Continued)

*Primary Examiner*—Yelena G Gakh
*Assistant Examiner*—David Weisz

(57) ABSTRACT

An apparatus for opening and closing a container having a slidable shutter closure moving past the apparatus includes: a rotatable shaft having an axis perpendicular to the direction of travel of the slidable shutter, the shaft being biased against rotation in either direction; a driver for bidirectionally moving the shaft from a position away from the container to a position in the vicinity of the container for opening and closing; and an extension extending outwardly from the rotatable shaft along at least a portion of the shaft into a line of travel, whereby the extension is adapted to engage the shutter closure of the container and move the shutter closure from an open position to a closed position or from a closed position to an open position. A reagent source for an automated analyzer includes: a reagent source which includes a container having a shutter closure which slides between an open and closed position; an apparatus for opening and closing the container. The apparatus includes: a rotatable shaft having an axis perpendicular to the direction of travel of the slidable shutter, the shaft being biased against rotation in either direction; a driver for bidirectionally moving the shaft from a position away from the container to a position in the vicinity of the container for opening and closing; and an extension extending outwardly from the rotatable shaft along at least a portion of the shaft, whereby the extension is located to engage the shutter closure of the container as the container is transported past the extension; and a bidirectional conveyor for transporting the container into engagement with and past the apparatus for opening and closing.

8 Claims, 3 Drawing Sheets

U.S. PATENT DOCUMENTS

| | | | |
|---|---|---|---|
| 5,167,172 A | | 12/1992 | Heebner |
| 5,578,494 A | * | 11/1996 | Clark et al. .................. 436/54 |
| 5,582,222 A | * | 12/1996 | Riall .......................... 141/346 |
| 6,866,820 B1 | * | 3/2005 | Otto et al. .................... 422/63 |

FOREIGN PATENT DOCUMENTS

| | | |
|---|---|---|
| EP | 0703457 | 3/1996 |
| EP | 0734963 | 10/1996 |
| EP | 1498183 | 1/2005 |

OTHER PUBLICATIONS

MicroPatent Search Search Scope: US Granted US Applications EP-A EP-B WO JP (bibliographic data only) DE-C,B DE-A GB-A; Full patent spec. Years 1971-2004 Text: ("bottle seal" or "bottle closure") and rotation and opener.

U.S. Appl. No. 09/482,599, filed Jan. 13, 2000, Bower.

"Service Manual for the *Vitros* ECi Immunodiagnostic System—Reagent Supply", Ortho-Clinical Diagnostics, Publication No. SM3354-6, Apr. 5, 2001, pp. 1-84.

* cited by examiner

OPENING AND CLOSING A CONTAINER

BACKGROUND OF THE INVENTION

The present invention relates to opening and closing a container having a slidable shutter type closure. In particular, the present invention relates to opening and closing a reagent pack on an automated analyzer.

Known diagnostic analyzers include immunodiagnostic and clinical chemistry analyzers such as the Vitros® ECi immunodiagnostic analyzer, sold by Ortho-Clinical Diagnostics, Inc. These types of analyzers include a source of reagents for carrying out various tests. Most often, the reagents are stored in containers having removable closures, which are opened and closed each time the reagent is accessed to limit evaporation and provide on-analyzer storage stability. For example, a reagent pack container as shown in FIG. 1 is used on the Vitros® ECi immunodiagnostic analyzer, sold by Ortho-Clinical Diagnostics, Inc. The shutter closure on the container shown in FIG. 1 is opened and closed by an opener that is positioned over the shutter closure. In operation, the opener lowers over the shutter, engages the shutter and rotates to open the container. This type of opener is described in "Service Manual for the Vitros ECi Immunodiagnostic System—Reagent Supply," Publication No. SM3354-6, published Apr. 5, 2001 by Ortho-Clinical Diagnostics, Inc., which is incorporated by reference in its entirety. In addition to having a relatively complex design, this type of opener requires the reagent pack container to be moved into position and come to a complete stop. The opener then engages the stopped reagent pack to open the pack. The pack is then rotated to a reagent metering station where reagent is aspirated using a reagent aspirate probe. The reagent pack is then rotated back to the opener, where the opener engages the shutter closure and closes the reagent pack.

In diagnostic analyzers, the throughput of an analyzer, i.e., the number of tests performed per hour, provides an important competitive advantage. However, the analyzer is only as fast as its slowest system. For example, if an incubator of an analyzer can process 180 tests/hr, but the reagent supply can only supply reagent for 90 tests/hr, then the system will necessarily be limited to 90 tests/hr.

With the known opener described above, the speed of accessing the reagents is limited (and thus the throughput of the analyzer is limited) due to requirement that the reagent pack be stopped to in order for the opener to engage the shutter opener/closure. Amongst other factors, such as the necessity to wash reagent metering probes, etc., the slow opening of a reagent pack contributes to the overall slowness of reagent metering. For example, the current process used to open and close these packs takes 8 seconds. In the current system using non-disposable reagent metering, the 8-second pack open/close time is not significant because it is done while the reagent-metering probe is being washed. With the disposable tip reagent-metering system being advantageous, the probe wash is eliminated which eliminates the available time to open and close the pack without causing a delay in assay processing. With the disposable tip reagent metering system, the pack opening and closing becomes the roadblock to improved throughput.

Other known openers include those described in U.S. Pat. Nos. 5,167,172 and 4,762,029 for opening and closing containers.

None of the known art described above, adequately addresses resolving the problems described above, in particular, of opening and closing containers in a relatively simple, efficient and quick manner. For the foregoing reasons, there is a need for a container opener that is relatively simple, efficient and can quickly open and close a container.

SUMMARY OF THE INVENTION

The present invention is directed to a method that solves the foregoing problems of reducing the time to open and close a container.

One aspect of the invention is directed to an apparatus for opening and closing a container having a slidable shutter closure moving past the apparatus. The apparatus includes: a rotatable shaft having an axis perpendicular to the direction of travel of the slidable shutter, the shaft being biased against rotation in either direction; a driver for bidirectionally moving the shaft from a position away from the container to a position in the vicinity of the container for opening and closing; and an extension extending outwardly from the rotatable shaft along at least a portion of the shaft into a line of travel, whereby the extension is adapted to engage the shutter closure of the container and move the shutter closure from an open position to a closed position or from a closed position to an open position.

Another aspect of the invention provides a reagent source for an automated analyzer which includes: a reagent source which comprises a container having a shutter closure which slides between an open and closed position; an apparatus for opening and closing the container. The apparatus includes: a rotatable shaft having an axis perpendicular to the direction of travel of the slidable shutter, the shaft being biased against rotation in either direction; a driver for bidirectionally moving the shaft from a position away from the container to a position in the vicinity of the container for opening and closing; and an extension extending outwardly from the rotatable shaft along at least a portion of the shaft, whereby the extension is located to engage the shutter closure of the container as the container is transported past the extension; and a bidirectional conveyor for transporting the container into engagement with and past the apparatus for opening and closing.

Yet another aspect of the invention provides an automated analyzer, which includes: a sample supply source; a sample metering station; a reaction vessel; a reagent source as described above; and a measuring instrument for measuring a property of the sample.

Still another aspect of the invention provides a combination container and container opener, which includes: a container having a slidable shutter closure; an apparatus for opening and closing the container. The apparatus includes: a retractable rotatable shaft having an axis perpendicular to the direction of travel of the slidable shutter, the shaft being biased against rotation in either direction; and an extension extending outwardly from the rotatable shaft along at least a portion of the shaft, whereby the extension is adapted to engage the shutter closure of the container.

Yet another aspect of the invention provides a method for opening or closing a container, which includes: providing a container having a shutter closure in a closed position slidable to an open position or in an open position slidable to a closed position; providing an apparatus for opening and closing the container, the apparatus includes: a rotatable shaft having an axis perpendicular to the direction of travel of the slidable shutter, the shaft being biased against rotation in either direction; a driver for bidirectionally moving the shaft from a position away from the container to a position in the vicinity of the container for opening and closing; and an extension extending outwardly from the rotatable shaft along at least a portion of the shaft into the line of travel of the conveyor at a neutral position; transporting the container in a first direction toward the apparatus; engaging the extension with the shutter closure as the container moves past the apparatus, whereby the extension forces the closure to slide from a closed to an open position or from an open position to a closed position.

Further objects, features and advantages of the present invention will be apparent to those skilled in the art from detailed consideration of the preferred embodiments that follow.

DETAILED DESCRIPTION OF PREFERRED EMBODIMENTS

Figure 1:
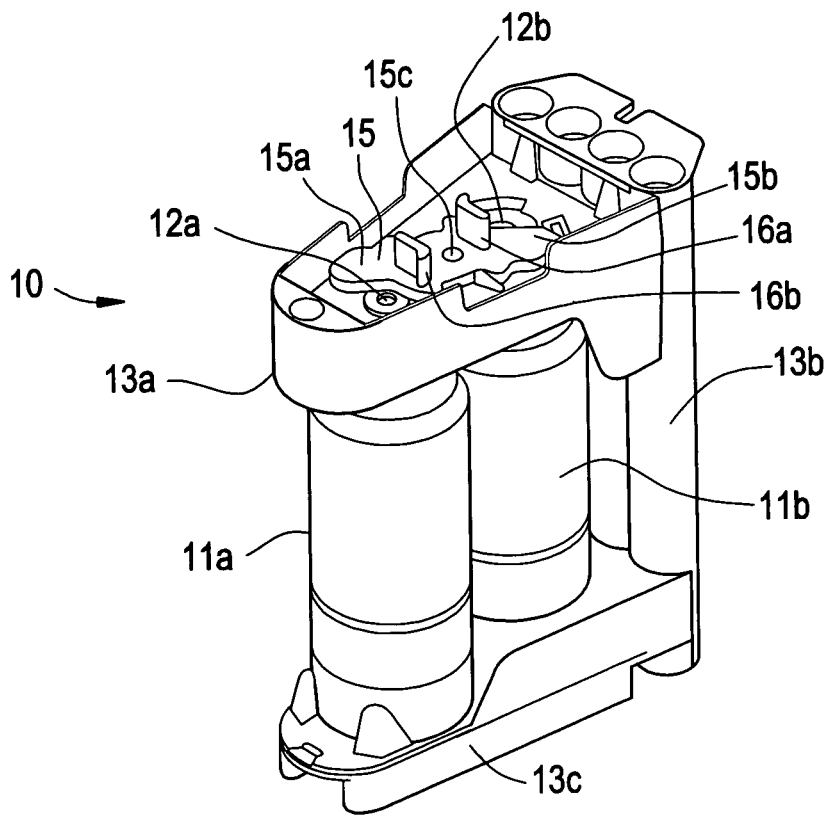
FIG. 1 is a perspective view of a reagent pack container known in the art.

The present invention includes an opener which has a simplified design for quick and dependable opening of a container which has a slidable shutter closure, such as that shown in FIG. 1. The simplified design is provided is by using the motion of the container to provide the necessary force to open or close the container, depending on its position.

Broadly, the opener includes a rotatable and axially translatable shaft. The axis of the shaft is approximately perpendicular to the direction of travel of the shutter opening. In most cases, this will be perpendicular to the direction of travel of the container. Attached to or extending from at least a portion of the shaft, preferably the end of the shaft closest to the container, is an extension which engages the shutter closure and provides the force necessary to open and/or close the shutter closure. The extension can be fashioned as a paddle or a fin and be a relatively flat extension having a relatively large surface area to engage the shutter closure.

When not engaged with the closure the extension is in a neutral position. However, since the shaft is rotatable, the extension is capable of being moved away from the neutral position when it is engaged with the closure. To return the extension to the neutral position, a biasing force, for example, provided by dual acting torsion springs, is provided which applies a force against the extension when the extension is away from the neutral position. This ensures that the extension is returned to its proper neutral position each time after engagement to provide proper alignment for engagement with the next container closure. Of course, since the apparatus is capable of opening and closing, it is necessary that the extension be moved or deflected in both directions and that the biasing force can return it to the neutral position from either deflected position.

As described above, the shaft is axially translatable. That is, it can be moved along the length of its axis. In those preferred embodiments, the extension can be moved away from the shutter closure of the container, when it is desired to not open the container. The shaft can be moved axially or translated by any suitable force, such as provided by a solenoid, a servo motor or pneumatic or hydraulic actuation systems.

The opener can be used with any suitable container having a closure that can be engaged with the extension, and which opens or closes by interaction of the extension and closure with the movement of the container providing the opening and closing force. In a preferred embodiment, the closure of the container is a shutter-type closure where the opening of the container is exposed by the closure sliding across the opening. To assist in engagement with the extension, a protrusion is provided that extends from the closure surface.

In a preferred embodiment, the container can be a reagent pack as shown in FIG. 1 and the protrusions are ribs that extend perpendicularly from the shutter closure to provide contact with the extension of the opener. The ribs must be positioned so they will provide sufficient time of contact so that as the container passes past the extension, the ribs will contact the biased extension which will force the slide closure to move either into an open or closed position depending on the direction of travel of the container.

In a preferred embodiment, the containers are used to hold reagents on a diagnostic analyzer. The reagent containers can be located and stored on the analyzer, preferably in a refrigerated condition for greater stability. In a preferred embodiment, the containers are located on a carousel that is capable of moving the containers past and into contact with the opener of the present invention, as well as the reagent metering system. Of course, a linear conveying system could also be used.

Now reference will be made to the non-limiting preferred embodiments shown in the figures. FIG. 1 is a known reagent pack container 10 used on diagnostic analyzers such as the Vitros® ECi analyzer described above. As FIG. 1 shows, the container includes two reagent bottles 11a and 11b having openings 12a and 12b, respectively. A frame 13a, 13b and 13c are used to contain the reagent bottles and to provide support for the slidable shutter. The vertical support 13b can be constructed in a tubular fashion in order to hold reaction wells. A sliding shutter closure 15 is mounted on the top of the reagent pack 10. In the embodiment according to FIG. 1, a single bifurcated slidable shutter having two sections 15a and 15b is used for each opening 12a and 12b, respectively. The shutter is rotatably anchored to the reagent pack by pin 15c.

Figure 2:
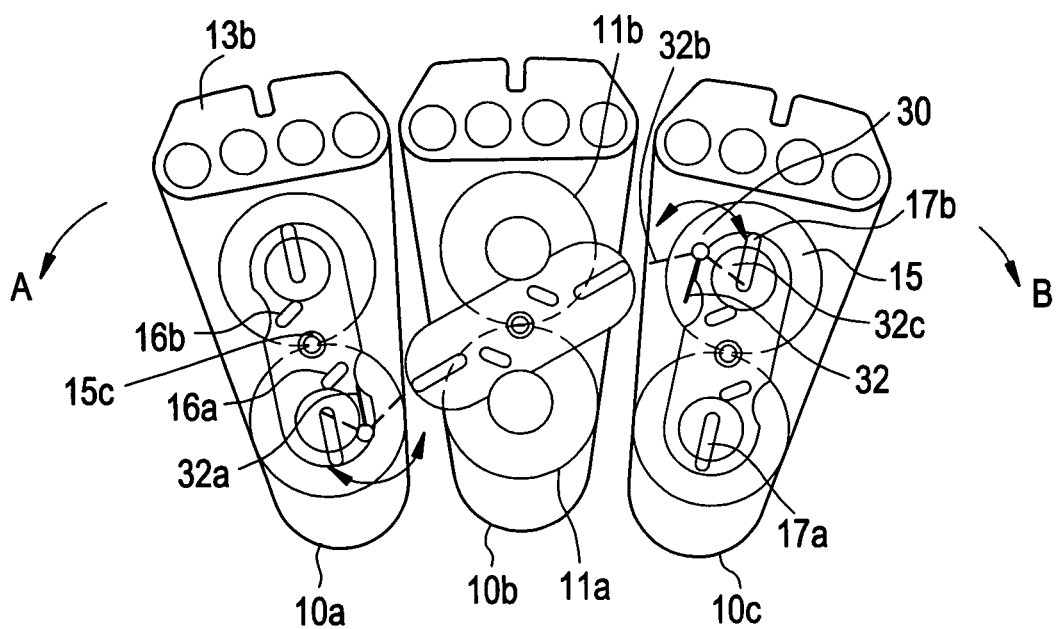
FIG. 2 is a top schematic view of a reagent pack and opener according to a preferred embodiment of the present invention.

A reagent pack according to FIG. 1 which has been modified along with the opener according to the present invention, is shown in FIG. 2. FIG. 2 is a top view of three side-by-side reagent packs on a carousel tray (not shown in FIG. 2). The reagent packs are similar to those shown in FIG. 1 and like reference numbers denote like features. One significant difference between the reagent pack in FIG. 1 and those shown in FIG. 2 is the addition of additional ribs 17a and 17b. These additional ribs allow the opener(s) 30 shown in the FIG. 2 embodiment to engage the shutter closure 15. The original ribs 16a and 16b are preferably retained to allow the modified reagent pack to be used on diagnostic analyzers that do not include the opener of the present invention.

Figure 3:
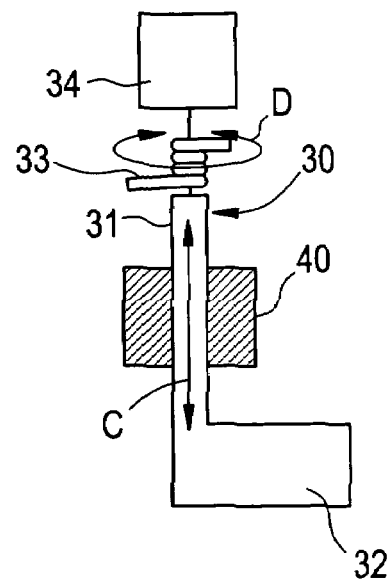
FIG. 3 is a side cross sectional view of the opener according to a preferred embodiment of the present invention.

The packs can move in both a clockwise direction B and a counterclockwise direction A as shown by the arrows in FIG. 2. Also shown in FIG. 2 are two openers 30 one each located on both sides of the reagent packs. As shown in FIG. 3, the opener includes an axially movable shaft 31 that can be moved in an direction shown by arrow C. The shaft 31 can also rotate about its axis in a direction D as also shown in FIG. 3. The opener also includes an extension 32 that extends away from the axis of the shaft. The extension can have any desired shape or configuration as long as it is capable of interacting with the ribs 17a and 17b. Preferably, the extension is in the shape of a paddle or blade, i.e., having a large planar surface area, relative to its thickness.

The opener can be mounted above or below the reagent packs as long as the extension 32 can interact with the ribs on the reagent pack. Preferably, it is mounted above the reagent packs. As shown in FIG. 3, the opener is mounted above the reagent packs using bracket or journal 40 that can be attached to any suitable part of the analyzer. As explained above, the shaft 31 can be axially translatable by any suitable force described above. In a preferred embodiment, the force can be a stepper motor 34 located at the top of the shaft 31. The motor is controllable to raise and lower the extension 32 into and out of contact with the reagent packs. This feature is useful when it open and closing of the reagent packs is not necessary, but rotation of the reagent packs past the opener(s) is necessitated.

As also explained above, while the extension is rotatable in both directions about shaft 31, it is biased against doing so by the action of a biasing force provided by a dual acting torsion spring 33. When no force is being applied to the extension, the extension is in a neutral position 32a which extends into the path of travel of the reagent pack. When the reagent pack engages the extension, the extension is moved into deflected positions 32b or 32c shown by phantom lines in FIG. 2. After disengagement, the spring 33 biases the extension back into its neutral position.

Figure 4:
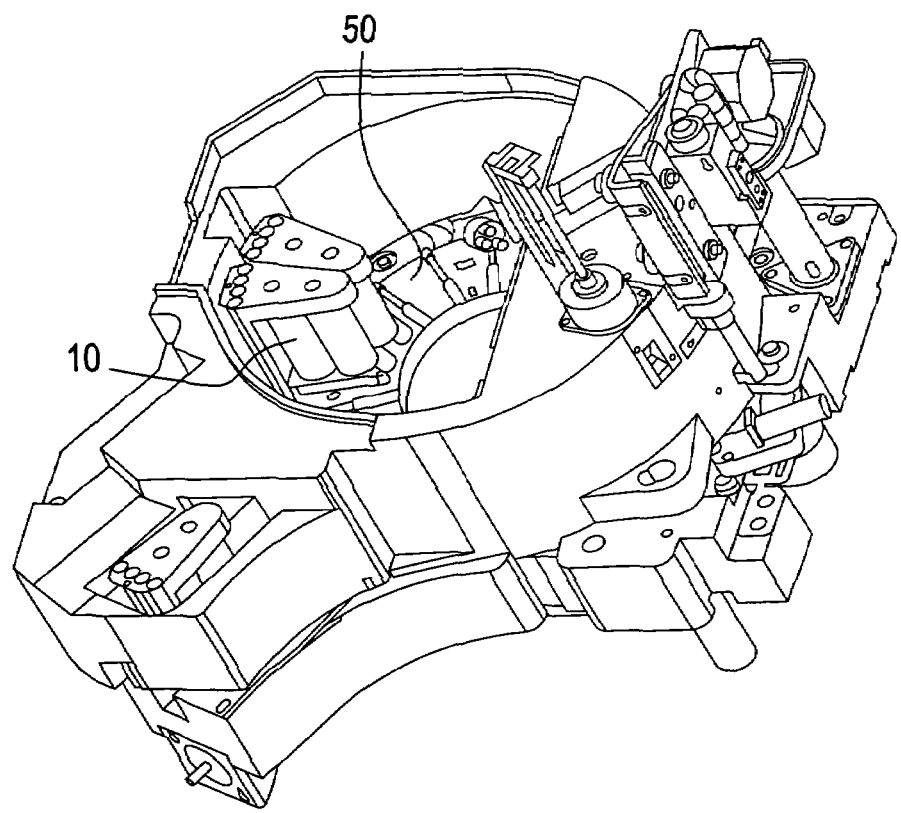
FIG. 4 is a perspective view of a reagent storage unit usable with the present invention, showing a carousel for rotating the reagent packs.

FIG. 4 shows the reagent packs in a reagent storage unit of a clinical analyzer. The reagent packs 10 (slidable shutter closures not shown) are located on a conveyor 50, which rotates the reagent packs past reagent pack opener(s) (not shown in FIG. 4).

In operation, the extension 32 is lowered by servo motor into the line of travel of the reagent packs 10 on conveyor 50. If the reagent packs are traveling in direction B as shown in FIG. 2, rib 16a will contact extension 32 in its neutral position 32a. Upon contact, extension 32 will deflect or move by rotation to towards position 32b. Due to the biasing force, the shutter opener will also deflect rotating the shutter around pin 15c. As the conveyor continues to rotate, the extension will then contact rib 17a, further deflecting the extension towards position 32b and further rotating shutter around pin 15c. After the extension disengages rib 17b, the extension returns to its neutral position and the shutter opening will be in its open position as shown by reagent pack 10b. Reagent may then be aspirated from the reagent pack by reagent metering probe 100 described below in connection with FIG. 5.

Closing the reagent packs will operate in much the same way as opening. When an open pack is transported on conveyor 50 in direction A as shown in FIG. 2, the extension in its neutral position 32a will contact rib 17b. As the reagent pack moves, extension 32 is deflected by rotation about shaft 31 towards position 32c. The shutter opening will also deflect and rotate around pin 15c towards a closed position. As the conveyor continues to rotate in direction A, the extension will contact rib 16 further rotating shutter opening towards closed position. Upon disengagement of the extension 32 from ribs 16, the extension 32 will return to neutral location 32a.

Figure 5:
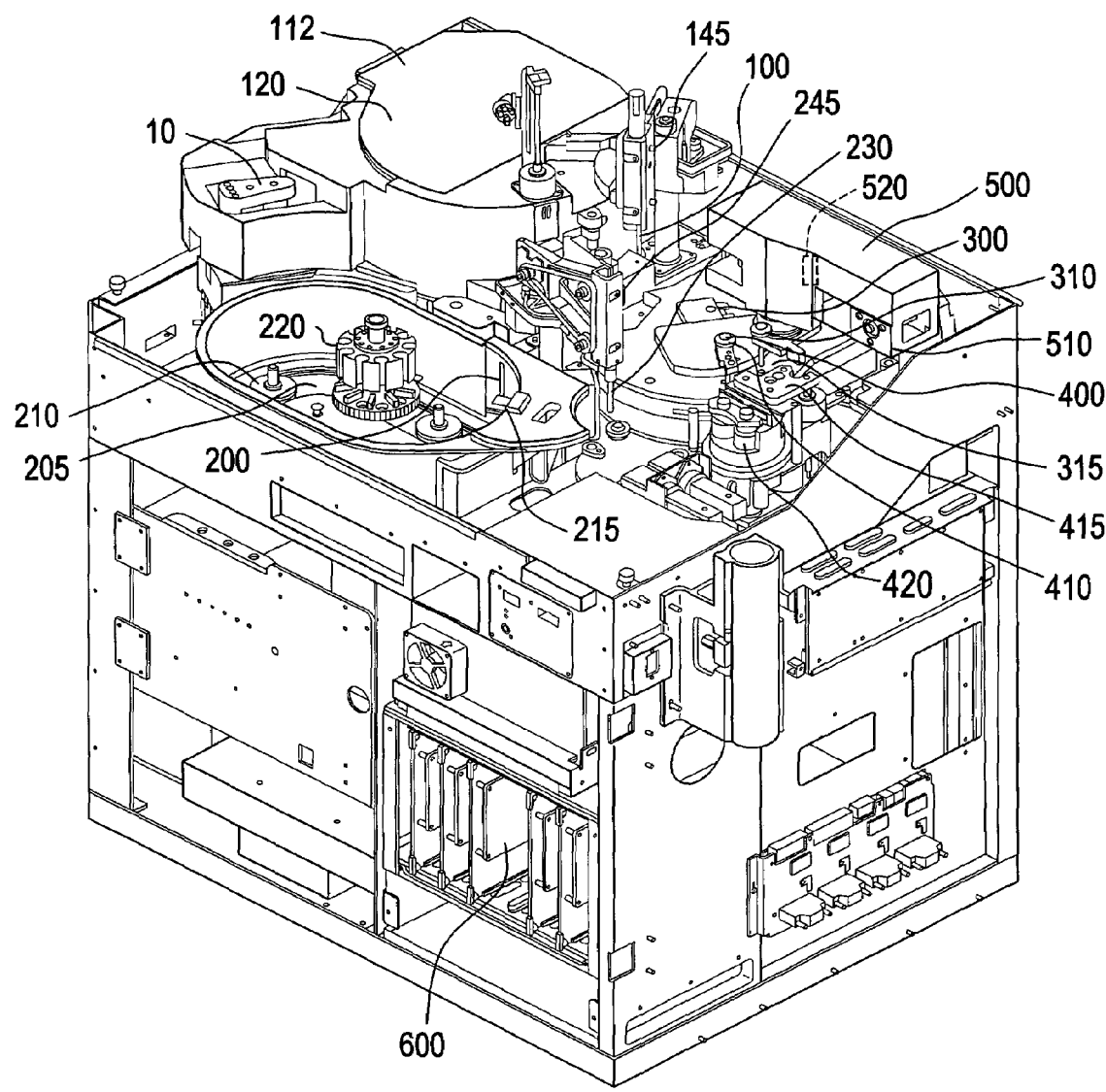
FIG. 5 is a perspective view of a diagnostic analyzer usable with the present invention.

FIG. 5 shows a preferred clinical analyzer that can be used the opener/closer of reagent packs according to one embodiment of the present invention. The type of analyzer is described in more detail in U.S. Ser. No. 09/482,599 filed Jan. 13, 2000, the contents of which are incorporated by reference. As shown in FIG. 5, reagent packs 10 are initially external to the system but they are components that are manipulated by the reagent source. Reagent packs 10 are configured to contain the reagents necessary to conduct an assay. Typically, they include one or more antigenic or antisera components used to combine with the analyte and provide adhesion to or with a reaction vessel.

The reagent source includes autoload station 110 which shuttles reagent packs to the reagent supply substation 112 by any suitable drive mechanism such as a chain and sprocket, belt and pulley, gear train, linked belt mechanism, a driven series of mechanical links such as pawl links, or the like. The reagent source further includes a reagent supply cooler 120 that cools the interior of the reagent supply substation according to the functional requirements of the reagents (typically, 3-15° C., preferably 4-10° C.). In this way, reagent supply cooler 120 maintains reagents and reaction vessels at the appropriate humidity and temperature.

The reagent source further includes a reagent metering arm 145 having a reagent probe 100 movably attached to it. Reagent metering arm 145 is pivotable so that it can position the reagent probe 100 in position to dispense reagent or diluent into a reaction vessel. Reagent probe 100 aspirates, transports, and dispenses reagent and/or diluent into reaction vessel. It is generally configured so that it also moves in a vertical direction to dip into the opened reagent packs 10 and lower itself into the vicinity of the reaction vessel (well). This is accomplished by any of the well known mechanisms for affecting vertical motion such as gear train with step motor, belt and pulley assembly, pneumatic or hydraulic lifts, or the like. A stepper motor with fine steps (at least about 390 steps per cm of vertical motion are desired) connected to a rack and pinion drive is the preferred mechanism for regulating vertical motion. Where pivoting is required, a stepper motor with fine steps is also preferred (generally, at least about 1720 steps per revolution of the shaft used to rotate the probe or probe arm are desired) with the pinion comprising or attached to the outer diameter of the shaft that is rotated. Control of stepper motors, and hence probe and mechanism movement, is accomplished by techniques well known in the art such as those described in U.S. Pat. No. 5,646,049 which is incorporated herein by reference.

In operation, the reagent probe 100 aspirates and dispenses fluids via connection to a fluidics systems comprised of valves, pumps, tubing, and the like. It is preferably charged by vacuum and can disperse by release of vacuum or by pressurization.

Sample supply source loads and meters sample to the appropriate reaction vessels (preferably, wells not shown). It is also capable of providing input to the data processing systems via bar code reader 200 that reads bar codes that may be placed on patient sample vessels such as test tubes and the like. The sample supply source also includes a number of subsystems and components. The sample supply subsystem is one which is comprised of a bar code reader 200 for inputting sample identification data as described above and a sample tray conveyor 205, one or more sample tray transports 210, and positioner 215 for moving sample to the sample metering station adjacent to the sample positioner (i.e. the position into which proboscis 230 is lowered, as described below).

The sample tray conveyor 205 can be any conveyor system for moving vessels and can employ an electrically or mechanically movable magnetic drive that propels a carousel 220 atop a sample tray transport 210 having a magnetic or ferrous component attractive to the magnetic drive. Alternatively, the sample tray conveyor 205 can comprise a motor driven chain and sprocket mechanism, a driven series of mechanical links such as pawl links, a belt driven system or the like. The preferred sample tray conveyor is an elliptical magnetically driven tracked system. In this system, the sample tray is preferably a carousel 220 that sits atop a transport 210 that has a piece susceptible to magnetic attraction. This enables it to be moved around the ellipse through the rotation of a magnetic field around the perimeter of the elliptical track from a position beneath the sample trays. In this configuration, the outer diameter of the sample tray can be geared so that the tray can be rotated about its own central axis by a geared piece such as positioner 215 adjacent to the bar code reader 200 (or at any other convenient location around the exterior of the elliptical track).

The sample metering subsystem aspirates samples and dispenses them into reaction vessels via proboscis 230. The proboscis and its related metering arm 245 are preferably similar in design to the reagent metering arm 145 described above. Disposable tips (not shown) through which sample can be aspirated and dispensed are preferably fitted on the proboscis and are disposed after use. The tips are preferably conical with the apex of the cone pointed toward down. Appropriate robotic commands are used to position the proboscis over the tips and then temporarily attach the tips via force (injection of the proboscis into the hollow portion of the tip). For convenience, a supply of tips can be maintained on a tip supply carousel (not shown). The tips can likewise be removed by raising the proboscis drive to its top most travel, activating an ejector sleeve (not shown). Generally, disposable tips are comprised of a molded thermoplastic such as polyethylene or polypropylene. Such tips avoid direct and repeated contact of sample and a singular proboscis end.

In operation, the sample metering subsystem functions similarly to that of the reagent metering system. Sample, loaded on sample carousel 220 is driven to a location reachable by the proboscis 230. After having loaded a disposable tip onto the proboscis, the system pivots the proboscis directly overhead a sample vessel. The proboscis is then lowered into a vessel such as a tube on the carousel where it aspirates a quantity of sample sufficient for the assay to be conducted. The proboscis is then pivoted to a position that is overhead a well residing in outer ring (not shown) where the sample is dispensed. It is preferable that the sample is dispensed into the well before reagent has been dispensed into the well. The proboscis can then be used to validate the proper metering of the sample into the well. This is accomplished by fitting the proboscis with a sensor such as an optical sensor on sample metering arm 245. The sensor (not shown) is in communication with a transducer (not shown) and the data processing system 600. The sensor preferably detects the level of the sample by pressure differential, through capacitance, or reflected energy as is known in the art. An optical sensor can also be used to home the proboscis to its proper position. After metering and measuring the sample, reagent is preferably dispensed into the well as described above. Mixing of sample and reagent is accomplished by dispensing reagent into the well containing sample with sufficient velocity to give partial mixing.

Some assays require dilution of the sample. When this is the case, sample is first metered into a dilution vessel that is preferably substantially similar to the wells previously described except that they are not generally treated with any reagent or other materials to which added reagent will adhere. That is, they are functionally inert within the context of the immunochemical reactions of interest. Proboscis 230 is used to meter the sample as in other assays.

In the processing system, reaction wells containing sample, reagent, and (optionally) diluent are mixed with signal reagent and incubated in incubator 300. Chemiluminescence or other appropriate signal generation of the reaction of sample analyte and reagent(s) is also read in this system. Well wash arm 310 and well wash probe 315 are the principle components of the well wash subsystem whose function is to wash the wells and remove sample and unbound reagent (analyte is bound to the reaction vessel along with reagents that manifest the signal that is read later). The temperature and humidity are controlled within incubator 300 for a time and at a temperature appropriate to the assays being performed. Incubation time can differ from assay to assay and is under the control of the data processing system.

Returning to the well wash subsystem, after appropriate incubation, well wash probe 315 (which is preferably similar in design to the reagent probe 100) is manipulated so that it aspirates and dispenses sample and unbound reagent out of the reaction wells and then dispenses wash fluid into the wells, aspirates and dispenses again. Thus, to this point within the reaction wells, reagent and analyte have reacted and have been adhered to the well. The well wash arm has removed materials that have not reacted and/or could otherwise interfere with sample reading.

It is also possible to configure such an instrument so that the unmeasured materials would adhere to a reaction vessel and the contents of the vessel would be further processed or be subject to some reading. In such a case they would then have to be aspirated and dispensed to another vessel.

Upon completion of well washing, the well wash arm 310 articulates movably attached well wash probe 315 to a position to aspirate sample and unbound reagent and dispense wash fluid to the reaction vessel. Generally, wash fluid is dispensed as the well wash probe 315 is lifted out of the reaction vessel. The signal reagent subsystem comprises signal reagent arm 410, signal reagent probe 400, signal reagent (packs) 420, and prime/pump assembly 415 as its major components. Signal reagent probe 400 (which is preferably similar in design to the other probes already described), movably attached to signal reagent arm 410 aspirates, transport, and dispenses signal reagent from signal reagent pack 420 to the wells. Signal reagent arm 410 is fitted to a prime, pump assembly 415 for this purpose. Signal reagent is a composition that contains a component that produces a signal upon combination with the reacted reagent/sample combination (e.g., luminol derivatives). Luminometer 500 is comprised of a fiber optic bundle 510 that communicates with photomultiplier 520 which is in further communication with data processing system 600. In operation, the fiber optic bundle 510 is positioned over the sample with mixed reagent and, optionally, diluent. Chemiluminescent signals generated by the reacting reagent/sample combination are then transmitted to the photomultiplier that converts the light signal to an electrical signal for processing according to conventional digital techniques. An internal reference (not shown) can be used for calibration of the luminometer 500.

Data processing system 600 is an integrated array of circuitry used to coordinate the function of the systems and subsystems, conduct system diagnostics, calibrate instrumentation, record results, and analyze results. It includes well known processing devices such as microprocessors and may be in electronic communication with any number of external processing systems. For example, it may be linked through a local area network to other analytical instrumentation so that tests are scheduled and results are compiled and reported for a number of different assays, some of which are not conducted on the instrument described here.

As described above, the advantages of the present invention as described above are in reducing the time required to open and close reagent packs for clinical analyzers. For example, in some embodiments, nearly all of the approximately 8 seconds needed for opening and closing reagent packs can be eliminated to reduce the reagent dispense timing cycle from 28 seconds to 20 seconds. This creates the potential to significantly increase the throughput speed of an analyzer. In the preferred embodiment described above in connection with the drawings, the reagent packs useable with the opener of the present invention can also be used on analyzers having prior openers, thus backwards compatibility is retained.

The opening and closing method according to the present invention can be implemented by a computer program, having computer readable program code, interfacing with the computer controller of the analyzer as is known in the art.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

We claim:

1. A reagent source for an automated analyzer comprising:
   a reagent source which comprises a container having a shutter closure which slides between an open and closed position;
   an apparatus for opening and closing the container, the apparatus comprising:
      a rotatable shaft having an axis perpendicular to the direction of travel of the slidable shutter, the shaft being biased against rotation in either direction;
      a driver for bidirectionally moving the shaft from a position away from the container to a position in the vicinity of the container for opening and closing; and
      an extension extending outwardly from the rotatable shaft along at least a portion of the shaft, whereby the extension is located to engage the shutter closure of the container as the container is transported past the extension; and
   a bidirectional conveyor for transporting the container into engagement with and past the apparatus for opening and closing.

2. A reagent source as claimed in claim 1, further comprising a torsion spring for biasing the shaft against rotation in either direction.

3. A reagent source as claimed in claim 1, wherein the action of the conveyor transporting the container provides the force for opening the container.

4. A reagent source as claimed in claim 1, wherein the conveyor is a turntable and the container is positioned on the turntable and the extension extends into the line of travel of the container.

5. A reagent source as claimed in claim 1, wherein the closure comprises protrusions to engage the extension.

6. A reagent source as claimed in claim 5, wherein the protrusions are ribs which vertically extend from the closure.

7. A reagent source as claimed in claim 1, wherein the closure includes a pin to anchor a portion of the closure and at least one free end which slides between the open and closed position and rotates around the pin.

8. A reagent source as claimed in claim 7, wherein the container has two chambers for separately holding two fluids, the openings of the containers are side-by-side and the pin to anchor a portion of the closure is located between the openings, and wherein the at least one free end includes two free ends on either side of the pin, each of the two free ends covering an opening of each of the containers.

* * * * *